(12) United States Patent
Stice et al.

(10) Patent No.: US 7,531,354 B2
(45) Date of Patent: May 12, 2009

(54) NEURONAL PROGENITORS FROM FEEDER-FREE HUMAN EMBRYONIC STEM CELL CULTURE

(75) Inventors: Steve Stice, Athens, GA (US); Soojung Shin, Baltimore, MD (US); Sujoy Dhara, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 143 days.

(21) Appl. No.: 11/243,819

(22) Filed: Oct. 5, 2005

(65) Prior Publication Data

US 2006/0073587 A1    Apr. 6, 2006

Related U.S. Application Data

(60) Provisional application No. 60/616,130, filed on Oct. 5, 2004, provisional application No. 60/616,183, filed on Oct. 5, 2004, provisional application No. 60/618,670, filed on Oct. 14, 2004.

(51) Int. Cl.
*C12N 5/00* (2006.01)
*C12N 5/06* (2006.01)

(52) U.S. Cl. .................. 435/325; 436/377; 436/363

(58) Field of Classification Search ................ 435/325, 435/377, 363
See application file for complete search history.

(56) References Cited

U.S. PATENT DOCUMENTS

| | | | |
|---|---|---|---|
| 6,576,464 B2 * | 6/2003 | Gold et al. | 435/325 |
| 6,833,269 B2 * | 12/2004 | Carpenter | 435/377 |
| 2005/0101014 A1 | 5/2005 | Keirstead et al. | |
| 2005/0196864 A1 | 9/2005 | Goldman et al. | |
| 2006/0211109 A1 | 9/2006 | Totey et al. | |

OTHER PUBLICATIONS

Lee et al. Nature Biotech. 18:675-679; 2000.*
Sonntag et al. Mol. Brain Res. 134: 34-51; 2005.*
Shin et al. Stem Cells 24:125-138; 2006.*
Li, X-J et al. "Specification of motoneurons from human embryonic stem cells" Nature Biotechnology Advance Online Publication (www.nature.com/naturebiotechnology).
Folkerth, J. Neuropath. Exp. Neuro., 58, 9, Sep. 1999).
Tenecza and Sipe, J. Appl. Toxicol., 24, 371-377 (2004).
Wichterle, et al., Cell, 110(3), 385-387 (2002).
Beck et al., FASEB J., 4(2):148-60 (Feb. 1, 1990).
Calhoun, et al., Boichem Biophys Res Commun., 306(1):191-197 (2003).
Carpenter et al., Cloning Stem Cells, 5(1), 79-88 (2003).
Carpenter et al., Dev. Dyn. 229(2), 243-248 (2004).
Cooper et al., J. Anat. 200(Pt. 3), 259-265 (2002).
Dang, et al., Biotechnol Bioeng. 78(4):442-453, (2002).
Draper et al., J. Anat. 200(Pt. 3), 249-258, (2002).
Engel, FEBS Lett. Jul. 17, 1989; 25(1-2):1-7 (Jul. 1989).
Folkerth, J. Neuropath. Exp. Neuro., 58, 9, Sep. 1999).
Gailani and Bate, J. Natr. Cancer Inst., 89(15), 1103-09 (1997).
Ginis et al. Dev. Biol. 269(2), 360-380 (2004).
Mitalipova, et al., Stem Cells, 21(5):521-526 (2003).
Novitch etal., Neuron, 31(5), 773-89 (2001).
Oka, et al., Mol. Biol. Cell, 13(4), 1274-81 (2002).
Reubinoff, et al., Nat Biotechnol. 19(12):1134-1140 (2001).
Rosler, et al., Dev. Dyn., 229(2): 259-74 (2004).
Tenecza and Sipe, J. Appl. Toxicol., 24, 371-377 (2004).
Wichlerle, et al., Cell, 110(3), 385-387 (2002).
Wu, et al., Nat. Neurosci., 5(12), 1271-78 (2002).
Ying et al., Nat Biotechnol. 21(2):183-186, (2003).
Zhang, et al., Nat. Biotechnol., 19(12), 1129-33 (2001).

* cited by examiner

*Primary Examiner*—Fereydoun G Sajjadi
(74) *Attorney, Agent, or Firm*—Henry D. Coleman; R. Neil Sudol; William J. Sapone

(57) ABSTRACT

The present invention relates to methods for producing feeder cell-free neuroprogenitor cells (preferably adherent) from embryonic stems cells, preferably human embryonic stem cells, the feeder cell-free neuroprogenitor cells, preferably human cells themselves, as well as methods for producing feeder cell-free samples of neuronal cells, preferably adherent human neuronal cells and the feeder cell-free neuronal cells themselves. Pharmaceutical compositions and methods of treating neurodegenerative diseases as well as the use of the described cells in assay systems is also described.

33 Claims, 3 Drawing Sheets

NEURONAL PROGENITORS FROM FEEDER-FREE HUMAN EMBRYONIC STEM CELL CULTURE

RELATED APPLICATIONS

This applications claims the benefit of provisional application Ser. Nos. 60/616,183, filed Oct. 5, 2004; 60/618,670, filed Oct. 14, 2004; and 60/616,130, filed Oct. 5, 2004, all of which applications are incorporated by reference in their entirety herein.

GOVERNMENT RIGHTS STATEMENT

This invention was made with government support under NIH/NINDS NS44208 awarded by the National Institutes of Health. The government has certain rights in the invention.

FIELD OF THE INVENTION

The present invention relates to methods for producing feeder cell-free neuroprogenitor cells from embryonic, preferably human embryonic stem cells, the feeder cell-free neuroprogenitor cells, preferably human cells themselves, as well as methods for producing feeder cell-free samples of neuronal cells, preferably human neuronal cells and the feeder cell-free neuronal cells themselves.

BACKGROUND OF THE INVENTION

Human embryonic stem (ES) cells are pluripotent cells isolated from developing blastocysts. ES cell culture requires feeder cells to support their growth, self renewal and maintenance of pluripotency. The most commonly used feeder cells in human ES cell culture are fibroblasts isolated from 13.5 days mouse embryos (MEF). One of the major goals of human ES cell research is to use differentiated derivatives of ES cells for cell therapies for diseases like Parkinson's. Use of feeder cells of nonhuman origin is a major hindrance for both diagnostic and clinical applications because of potential zoonotic transmission. Another challenge to neural stem cell therapies is generating pure populations of the cell type of interest. Undesired cell types, such as left over ES cells, may produce clinical complications. These adherent neuronal progenitors are more uniform than NP cell grown as neurospheres. However, that method still requires the use of MEF to derive the adherent progenitor cells. In the present report, we demonstrate for the first time that adherent NP cells can be derived from human ES cells without the use of feeder cells.

Embryonic stem (ES) cells serve as an excellent in vitro system for studying differentiation events and for developing methods of generating various specialized cells for future regenerative therapeutic applications.

The understanding of mammalian cellular differentiation and cell fate specification are progressing intensively using an in vitro system, comprised of embryonic stem cells. Research on the cell fate specification in the central nervous system is of enormous interest given the therapeutic potential in neuronal repair strategies.

Human ES Cell differentiation to neural cell stem cells have broad applications from potential cell therapies for anyone of 500 neurodegenerative diseases to use in drug discovery and toxicity assays for neurological applications. Already mouse ES cell studies have had promising results in transplant models as shown by their demonstration of efficacy in a rat model of Parkinson's Disease.

In addition, primate ES cells can play an important intermediate translational role as stem cell differentiation strategies are transitioned from rodent systems to human clinical applications. Clinical trials for human ES cells as a therapy will be greatly enhanced by data gathered in a primate transplant model. Primate and human ES cells share many characteristics, making primate ES cells an appropriate model in which to refine differentiation protocols for translational studies.

In order for neural progenitors to be used in clinical applications, their method of derivation must be scalable and free from contaminating cell types.

OBJECTS OF THE INVENTION

It is an object of the invention to provide methods for producing neuroprogenitor cells without the use of feeder cells.

It is an additional object of the present invention to provide for neuroprogenitor cell samples which are free from contamination of feeder cells.

It is still a further object of the invention to provide adherent neuroprogenitor cell samples which are free from contamination of feeder cells.

It is yet another object of the invention to provide a method to produce post mitotic neuronal cells or neuron motor cells from neuroprogenitor cells which is free from the use of feeder cells.

It is a further object of the invention to provide post mitotic neuronal cells which are free from feeder cells.

It is an additional object of the invention to provide pharmaceutical compositions comprising effective amounts or concentrations of neural progenitor cells or neuronal cells for use in research, including cell based assays for drug discovery, toxicity and for understanding basic developmental processes, for diagnostic applications and therapy including methods for treating neurodegenerative diseases, or brain or spinal cord injuries or damage.

It is another object of the invention to provide methods for isolating and inducing differentiation of embryonic stem cells, in particular, human embryonic stem cells to produce neuroprogenitor cells or neuronal cells which are free from feeder cells and which can be used in diagnostic and transplantation procedures or for the treatment of neurodegenerative diseases, brain or spinal cord injuries or damage.

One or more of these and/or other objects of the invention may be gleaned from a description of the invention which follows.

BRIEF DESCRIPTION OF THE INVENTION

Figure 1:
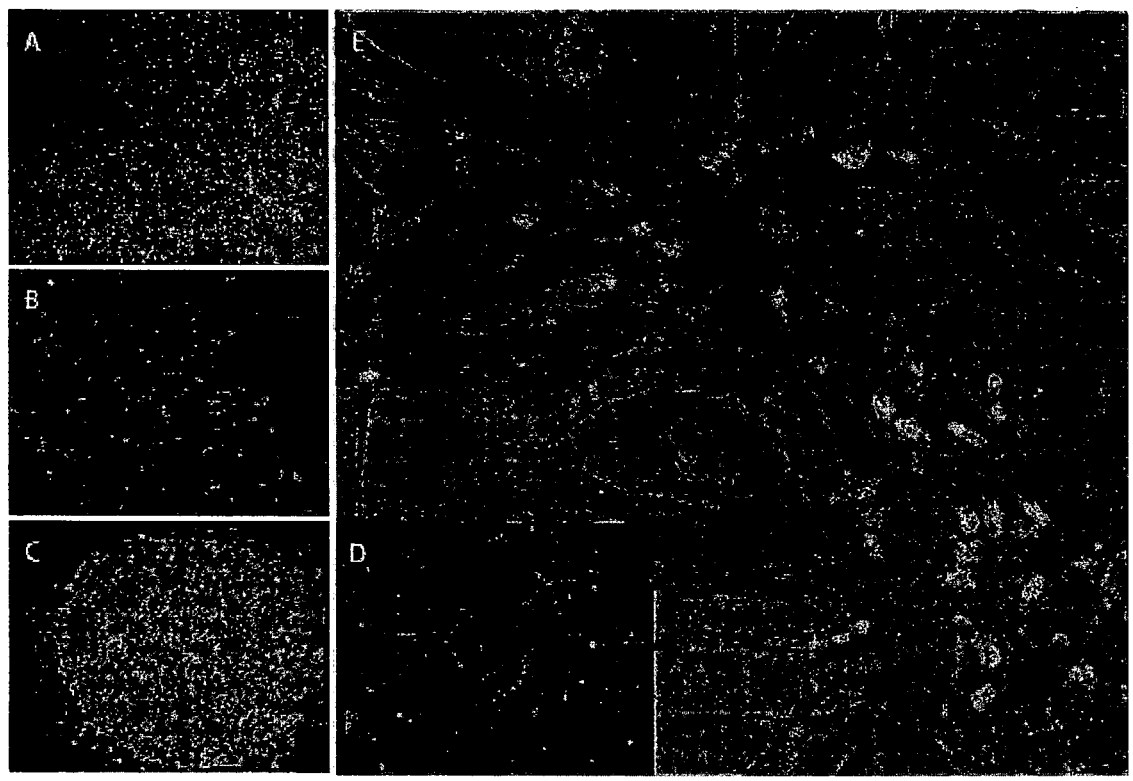
FIG. 1 shows (A) Phase contrast image of NEP. (B-C) Oct4 (red) and Nestin (green) expression in (B) NEP with no Oct4 expression and (C) HESC with Oct4 expression. (D-E) Motor neuron phenotype marker expression in differentiated NEP: (D) Choline Acetyltransferase (Red) and DAPI (Blue), (E) Islet1(green) and Tuj1 (red). Magnification: ×200.

In a first aspect, the present invention is directed to a method for producing feeder cell free neuroprogenitor cells, said method comprising the steps of:

1. Contacting embryonic stem cells in a cell medium comprising at least the components of a minimum essential medium (preferably a DMEM/F12 media or neurobasal media optionally containing L-glutamine, glucose and at least one antibiotic (penicillin and streptomycin, among others) and further optionally, at least one component selected from the group consisting of basic fibroblast growth factor (bFGF), knockout serum replacement (KSR), fetal bovine serum (FBS), non-essential amino acids, leukaemia inhibitory factor (LIF) and mercaptoethanol and another media such as B27, N2 or a related culture media) to an effective amount of at least one differentiation protein, preferably an extracellular matrix protein as described herein, preferably laminin, in the absence of feeder cells for a period of at least about 9 days, preferably at least about 15 days, preferably at least about 17 days and more preferably at least 21 days to differentiate said embryonic stem cells into neuroprogenitor cells; and
2. Optionally isolating or collecting said neuroprogenitor cells.

In the above method, neuroprogenitor cells may be optimally produced by using a preferred media, in particular DMEM/F12 (1:1) or neurobasal media, which may be supplemented with any one or more of L-glutamine, knockout seum replacement (KSR), fetal bovine serum (FBS), non-essential amino acids, leukeamia inhibitory factor (LIF), beta-mercaptoethanol, basic fibroblast growth factor (bFGF), an antibiotic, B27 medium supplement and/or N2 medium supplement. Isolation of the resulting neuroprogenitor cells or motor neuron cells is readily accomplished mechanically, for example, by using a laboratory spatula or pipette, in many instances, by simply breaking up the cells which are produced on the differentiation protein. Once collected, the cells may be isolated by centrifugation, propagated in fresh media or frozen through standard cryopreservation techniques and stored, or concentrated and placed in fresh media for further growth and/or propagation.

In another aspect of the invention, neuroprogenitor cells (NP cells) which are optionally produced above are exposed to cell culture medium (as described above) in the absence of feeder cells in the presence of an effective amount of fibroblast growth factor 2 (FGF2), optionally in the presence of effective amounts of Sonic Hedgehog, retinoic acid and/or LIF and the presence of an effective amount of a differentiation protein for a period of about 1 to 10 days, followed by a period of exposure to cell culture medium in the absence of FGF2, Sonic Hedgehog, retinoic acid or LIF or feeder cells for an additional period of about 5 to 20 days to produce motor neuron cells.

Other aspects of the invention relate to the neuropregenitor cells or motor neuron cells produced by the methods according to the present invention which are free from contaminating feeder cells and preferably are adherent cultures.

Thus, according to the present invention, a method is described for deriving from primate (monkey and human) embryonic stem cells (ESC) an enriched population of essentially pure neural progenitor (NP) cells which is cost effective and generally applicable, which method avoids the requirement for feeder cells/layers (is free from contaminating feeder cells), and additionally embryoid body formation, the inhibition of the bone morphogenic protein (BMP) signaling pathway, specific neural growth or conditioned medium such as MEDII by a two-step process of differentiation and subsequent mechanical purification. The present method is simple, economic and a clear advance in the art.

The NP cells obtained above can undergo induction towards motor neurons when exposed to various growth factors such as FGF2 (also known as basic FGF, bFGF or PFGF) which may optionally include Sonic Hedgehog and retinoic acid for 1 to 10 days followed by differentiation without inducting factors (FGF2, Sonic Hedgehog and/or retinoic acid) for another 5 to 20 days. At the end of the above-described period, cultures contain a relatively high number of motor neurons (quite often greater than 90-95%. In some cases >90% as determined via immunocytochemistry for Islet 1/2. It is noted here that in a preferred aspect of the invention, neural progenitor cells obtained above may be induced to motor neurons in the presence of fibroblast growth factor 2 (FGF2) without the addition of Sonic Hedgehog and/or retinoic acid, a cost savings which makes the present invention quite applicable to commercial approaches for producing motor neuron cells.

DETAILED DESCRIPTION OF THE INVENTION

The following terms are used within context to describe the present invention. Note that terms used to generally describe the present invention are used in a manner keeping with its common meaning as understood by one of ordinary skill in the art.

The term "embryonic stem cell" refers to pluripotent cells, preferably of primates, including humans, which are isolated from the blastocyst stage embryo. Human embryonic stem cell refers to a stem cell from a human and are preferably used in aspects of the present invention which relate to human therapy or diagnosis. The following phenotype markers are expressed by human embryonic stem cells:

SSEA-3, SSEA-4, TRA-1-60, TRA-1-81, GCTM-2, TG343, TG30, CD9,

Alkaline phosphatase, Oct 4, Nanog, TRex 1, Sox2, TERT and Vimentin. See Ginis, et al., *Dev. Biol,* 269(2), 360-380 (2004); Draper, et al., *J. Anat.,* 200(Pt. 3), 249-258, (2002); Carpenter, et al., *Cloning Stem Cells,* 5(1), 79-88 (2003); Cooper, et al., *J Anat.,* 200(Pt.3), 259-265 (2002); Oka, et al., *Mol. Biol. Cell,* 13(4), 1274-81 (2002); and Carpenter, et al., *Dev. Dyn.,* 229(2), 243-258 (2004). While any human stem cell can be used in the present methods to produce human neuroprogenitor cells and postmitotic neuronal cells, preferred human embryonic stem cells for use in the present invention include stem cells from the cell lines BG01 and BG02, as well as numerous other available stem cell lines.

The term "neuroprogenitor cells" or "neuroepithelial stem cells" is used to describe cells which are the earliest multipotent neural stem cells. These are self renewing cells that can differentiate into neurons, oligodendrocytes and astrocytes. Neuroprogenitor cells (NP) or (NEP) according to the present invention may be further delineated into "early neuroprogenitor cells" and "late neuroprogenitor cells". Early neuroprogenitor cells are neuroprogenitor cells which are freshly isolated without further propagation. Late neuroprogenitor cells are neuroprogenitor cells which have been propagated for at least about three months. In general, the present invention does not distinguish between early and late neuroprogenitor cells except with respect to the age of the cells, not their function or the production of neuron motor cells. Neuroprogenitor cells according to the present invention express markers associated with the earliest multipotent neural stem cells, including Nestin, a neural intermediate filament protein, Musashi-1, a neural RNA binding protein, as well as Sox1, Sox2 and Sox3, but these cells do not express further differentiation markers such as PSNCAM, MAPH, or other late stage neuronal or glial lineage markers such as A2B5/4D4, GFAP/CD44, RC1/S100/Vimentin, Sox10/NG2/PDGFRα, O4/GALC, PLP-DM20/CNP/MBP. In the present invention, the expression of Sox1, Sox2 and Sox3 in the absence of Oct4 is evidence of the existence of a neuroprogenitor cell.

The term "differentiation protein" is used to describe a protein which is included in cell media used to grow cells to promote differentiation (also preferably attachment) of a primate embryonic stem cell, in particular, a human embryonic stem cell into a neuroprogenitor cell according to the present invention "embryonic stem cell differentiation protein", or diffentiation of a neuroprogenitor cell into a motor neuron cell "neuroprogenitor differentiation protein". Embryonic stem cell differentiation proteins include for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting and differentiation activity. Other embryonic stem cell differentiation proteins which may be used in the present invention include for example, collagen, fibronectin, vibronectin, polylysine, polyomithine and mixtures thereof. In addition, gels and other materials which contain effective concentrations of one or more of these embryonic stem cell differentiation proteins may also be used. Exemplary embryonic stem cell differentiation proteins or materials which include these differentiation proteins include, for example, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others. The preferred embryonic stem cell differentiation protein for use in the present invention includes laminin.

A preferred composition/material which contains one or more differentiation protein is BD Matrigel™ Basement Membrane Matrix. This is a solubilized basement membrane preparation extracted from the Engelbreth-Holm-Swarm (EHS) mouse sarcoma, a tumor rich in ECM proteins. Its major component is laminin, followed by collagen IV, heparan sulfate, proteoglycans, entactin and nidogen.

Neuroprogenitor differentiation proteins which are used in the present invention include, for example, Fibroblast Growth Factor 2, preferably alone (because of the economic advantages associated with such use) or optionally combined with Sonic Hedgehog and/or retinoic acid in effective amounts.

The term "effective amount" is used throughout the specification to describe concentrations or amounts of components such as embryonic stem cell or neuroprogenitor differentiation proteins, embryonic stem cells, neuroprogenitor cells, neuronal cells, components of cell media or other agents which are effective for producing an intended result within the context of practicing one or more aspects of the present invention. Effective amounts are those which are generally known to those of ordinary skill in the art and are typically used when growing embryonic stem cells, neuroprogenitor cells and/or motor neuron cells.

The term "neuron cells" are postmitotic neuronal cells or motor neuron cells having a neuronal phenotype which expresses:

for pan-neural cells: MAP2, Tuj1, Hu, PSNCAM;

for motor neurons: HB9, Islet 1/2, ChAT and Olig2, oligo 04/GALC, A2B5/AD4;

for glia cells: GFAP/CD44, RC1/S100/Vimentin, Sox10/NG2/PDGFRα and PLP-DM20/CNP/MBP. These cells may be obtained from neuroprogenitor cells according to the present invention, indirectly from embryonic stem cells according to the present invention.

The table below summarizes some of the expression markers for neural lineages.

TABLE 1

Summary of Some Markers Expression for neural lineages (list not complete)

| Markers | Mouse NP[a] | Human NP[b] | Expression |
|---|---|---|---|
| SOX2 | + | + (>90%) | Neural stem (nuclear) |
| SOX1 | + | + | Neural stem (nuclear) |
| Musashi | | + (>90%) | Neural stem (nuclear) |
| Nestin | + | + (>90%) | Neural stem and Oligo precursors, others |
| EGFR | − | | Later appearing NSCs/Differentiated cells |
| E-NCAM | − | − | Neural specific precursors/Neurons |
| Tuj1 | − | − | Neurons/Neural specific precursors |
| MAP2 | − | − | Neurons/Neural specific precursors |
| Hu | − | − | Neurons |
| A2B5 | − | − | GRP/Oligodendrocyte precursors |
| O4 | − | − | Oligodendrocytes |
| Nkx2.2 | − | | GRP/Oligodendrocytes |
| GalC | − | | Oligodendrocytes |
| PDGFR | − | | Astrocytes/Oligodendrocytes/Neurons |
| GFAP | − | − | Astrocytes/Radial glia cells |

[a]Cai ert al., 2002
[b]Shin et al., 2005a

The term "administration" or "administering" is used throughout the specification to describe the process by which neural cells according to the present invention are delivered to a patient for treatment purposes. Neural cells may be administered a number of ways including parenteral (such term referring to intravenous and intraarterial as well as other appropriate parenteral routes), intrathecal, intraventricular, intraparenchymal (including into the spinal cord, brainstem or motor cortex), intracisternal, intracranial, intrastriatal, and intranigral, among others which term allows neural cells to migrate to the cite where needed. Administration will often depend upon the disease or condition treated and may preferably be via a parenteral route, for example, intravenously, by administration into the cerebral spinal fluid or by direct administration into the affected tissue in the brain. For example, in the case of Alzheimer's disease, Huntington's disease and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but will often be directly into the affected tissue (which may be readily determined using MRI or other imaging techniques).

The terms "grafting" and "transplanting" and "graft" and "transplantation" are used throughout the specification synonymously to describe the process by which neural and/or neuronal cells according to the present invention are delivered to the site within the nervous system where the cells are intended to exhibit a favorable effect, such as repairing damage to a patient's central nervous system, treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Neural cells for use in the present invention may also be delivered in a remote area of the body by any mode of administration as described above, relying on cellular migration to the appropriate area in the central nervous system to effect transplantation.

The term "essentially" or "substantially" is used to describe a population of cells or a method which is at least 90+% pure or at least 90+% effective, more preferably at least about 95+% pure and/or effective and even more preferably at least about 99+% pure and/or effective.

The term "non-tumorigenic" refers to the fact that the cells do not give rise to a neoplasm or tumor. Stem and/or progenitor cells for use in the present invention are generally free from neoplasia and cancer.

The term "cell medium" or "cell media" is used to describe a cellular growth medium in which embryonic stem cells, neuroprogenitor cells and/or neuronal cells are grown. Cellular media are well known in the art and comprise at least a minimum essential medium plus optional agents such as growth factors, including fibroblast growth factor, preferably basic fibroblast growth factor (bFGF), leukaemia inhibition factor (LIF), glucose, non-essential amino acids, glutamine, insulin, transferrin, beta mercaptoethanol, and other agents well known in the art. Preferred media include commercially available media such as DMEM/F12 (1:1) or neurobasal media, each of which may be supplemented with any one or more of L-glutamine, knockout seum replacement (KSR), fetal bovine serum (FBS), non-essential amino acids, leukeamia inhibitory factor (LIF), beta-mercaptoethanol, basic fibroblast growth factor (bFGF) and an antibiotic, B27 medium supplement and/or N2 medium supplement. Cell media useful in the present invention are commercially available and can be supplemented with commercially available components, available from Invitrogen Corp. (GIBCO) and Biological Industries, Beth HaEmek, Israel, among numerous other commercial sources. In preferred embodiments at least one differentiation agent is added to the cell media in which a stem cell or neuroprogenitor cell is grown in order to promote differentiation of the stem cells into neuroprogenitor cells and the neuroprogenitor cells into motor neuron cells. One of ordinary skill in the art will be able to readily modify the cell media to produce neuroprogenitor or motor neuron cells pursuant to the present invention.

The term "laminin" refers to a specific differentiation protein used in the present invention which includes multidomain glycoproteins which are the major noncollagenous components of basement membranes. Laminin has numerous biological activities including promotion of cell adhesion, migration, growth, and differentiation, including neurite outgrowth. Laminin can be used as a thin coating on tissue-culture surfaces or as a soluble additive to culture medium. Laminin has been shown in culture to stimulate neurite outgrowth, promote cell attachment, chemotaxis, and cell differentation.

Laminin is composed of distinct but related $\alpha, \beta$ and gamma chains. Laminin is a large (900 kDa) mosaic protein composed of many distinct domains with different structures and functions. Globular and rodlike domains are arranged in an extended four-armed, cruciform shape that is well suited for mediating between distant sites on cells and other components of the extracellular matrix. The alpha-helical coiled-coil domain of the long arm is involved in the specific assembly of the three chains (A, B1, B2, and possible variants) of laminin and is the only domain composed of multiple chains. It is terminated by a large globular domain composed of five homologous subdomains formed by the COOH-terminal part of the A chain. Sites for receptor-mediated cell attachment and promotion of neurite outgrowth reside in the terminal region of the long arm. A second cell attachment site, a cell signaling site with mitogenic action, binding sites for the closely associated glycoprotein nidogen/entactin, and regions involved in calcium-dependent aggregation are localized in the short arms. These domains, which to a large extent are composed of Cys-rich repeats with limited homology to EGF, are the most highly conserved regions in laminins of different origin. A preferred laminin for use in the present invention is that expressed by a mouse tumor, which can be readily isolated in native form and dissected into functional fragments by limited proteolysis. Increasing information on laminins from different species and tissues demonstrates considerable variations of structure. Isoforms of laminin assembled from different chains are focally and transiently expressed and may serve distinct functions at early stages of development even before being laid down as major components of basement membranes. In the present invention, all forms of laminins are useful, with laminin obtained from mouse tumor being preferred. See, Beck, et al., *FASEB J.*, 4(2):148-60 (Feb. 1, 1990); and Engel, *FEBS Lett.* 1989 Jul. 17;251(1-2):1-7 (July 1989).

The term "neurodegenerative disease" is used throughout the specification to describe a disease which is caused by damage to the central nervous system and which damage can be reduced and/or alleviated through transplantation of neural cells according to the present invention to damaged areas of the brain and/or spinal cord of the patient. Exemplary neurodegenerative diseases which may be treated using the neural cells and methods according to the present invention include for example, Parkinson's disease, Huntington's disease, amyotrophic lateral sclerosis (Lou Gehrig's disease), Alzheimer's disease, lysosomal storage disease ("white matter disease" or glial/demyelination disease, as described, for example by Folkerth, *J. Neuropath. Exp. Neuro.*, 58, 9, Sep., 1999), Tay Sachs disease (beta hexosamimidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. The term neurodegenerative diseases also includes neurodevelopmental disorders including for example, autism and related neurological diseases such as schizophrenia, among numerous others.

Neuroprogenitor cells and/or neuronal cells which result from differentiation of neuroprogenitor cells according to the present invention may be used for in vitro/in vivo studies or for therapeutic intervention. For example, these cells may be used to conduct studies on treatments for patients, in cellular based assay systems (immunocytochemistry, high throughput and content assays, etc.) to identify drugs or other agents which may be useful to treat neurological conditions, to effect a transplantation of the neuronal cells within a composition to produce a favorable change in the brain or spinal cord, or in the disease or condition treated, whether that change is an improvement (such as stopping or reversing the degeneration of a disease or condition, reducing a neurological deficit or improving a neurological response) or a complete cure of the disease or condition treated.

Neuroprogenitor cells and/or neuronal cells which result from differentiation of neuroprogenitor cells according to the present invention may be used for detection of toxins for homeland defense and in general neuotoxicity. Neurons are directly exposed to the substance of interest, thus potentially providing greater sensitivity to threats than that resulting from oral ingestion. The use of neurons is advantageous because they can provide not only a measure of the potential toxicity of a substance but also a warning that a substance has the capacity to influence neurobehavior.

The present invention may also be used in diagnostic/drug discovery applications, as well as the toxicology assays described above. In general, the present invention may be used to provide diagnostic assays for drug discovery, diagnostics for neurological diseases. In particular, the neuroprogenitor and/or motor neuron cells according to the present invention may be used to determine whether or nor a suspect agent is a neurotoxin (for example, by looking at cell death or the effect on the health of the cells) or an agonist or antagonist of calcium uptake (e.g., a calcium channel blocker) by measuring calcium concentration within the cells. Other approaches are also available. One approach which may be used to determine neurotoxicity of compounds using the cells of the present invention is the high-content assays of Tenecza and Sipe, *J. Appl. Toxicol.*, 24, 371-377 (2004).

Neuroprogenitor cells and/or neuronal cells according to the present invention, which are free from contaminating feeder cells, may be used for treating a neurodegenerative disorder or a brain or spinal cord injury or neurological deficit comprising administering to (preferably, transplanting in) a patient suffering from such injury, a neurodegenerative disorder or neurlogical deficit an effective amount of neuroprogenitor cells and/or neuronal cells according to the present invention. Neurodegenerative disorders which can be treated using the method according to the present invention include, for example, Parkinson's disease, Huntington's disease, multiple sclerosis (MS), Alzheimer's disease, Tay Sach's disease (beta hexosamimidase deficiency), lysosomal storage disease, brain and/or spinal cord injury occurring due to ischemia, spinal cord and brain damage/injury, ataxia and alcoholism, among others, including a number which are otherwise described herein.

Neuroprogenitor cells and/or neuronal cells according to the present invention may be used for treating neurological damage in the brain or spinal cord which occurs as a consequence of genetic defect, physical injury, environmental insult or damage from a stroke, heart attack or cardiovascular disease (most often due to ischemia) in a patient, the method comprising administering (including transplanting), an effective number or amount of neural cells obtained from umbilical cord blood to said patient, including directly into the affected tissue of the patient's brain or spinal cord. Administering cells according to the present invention to a patient and allowing the cells to migrate to the appropriate cite within the central nervous system is another aspect of the present invention.

Pharmaceutical compositions comprising effective amounts of neuroprogenitor and/or motor neuron cells are also contemplated by the present invention. These compositions comprise an effective number of neuroprogenitor cells and/or motor neuron cells, optionally in combination with a pharmaceutically acceptable carrier, additive or excipient. In certain aspects of the present invention, cells are administered to the patient in need of a transplant in sterile saline. In other aspects of the present invention, the cells are administered in Hanks Balanced Salt Solution (HBSS) or Isolyte S, pH 7.4. Other approaches may also be used, including the use of cellular media as otherwise described herein, preferably in the absence of growth facts. Such compositions, therefore, comprise effective amounts or numbers of neuroprogenitor or motor neuron cells in sterile saline. These may be obtained directly by using fresh or cryopreserved cells.

Pharmaceutical compositions according to the present invention preferably comprise an effective number within the range of about $1.0 \times 10^2$ neuroprogenitor and/or motor neuron cells to about $5.0 \times 10^7$ mononuclear cells, more preferably about $1 \times 10^4$ to about $9 \times 10^6$ cells, even more preferably about $1 \times 10^6$ to about $8 \times 10^6$ cells generally in solution, optionally in combination with a pharmaceutically acceptable carrier, additive or excipient. Effective numbers of neuroprogenitor and/or motor neuron cells, either within a sample of other cells or preferably, as concentrated or isolated cells, may range from as few as several hundred or fewer to several million or more, preferably at least about one thousand cells within this range. In aspects of the present invention whereby the cells are injected in proximity to the brain or spinal cord tissue to be treated, the number of cells may be reduced as compared to aspects of the present invention which rely on parenteral administration (including intravenous and/or intraarterial administration).

In using compositions according to the present invention, fresh or cryopreserved motor neuron cells may be used without treatment with a differentiation agent or neuroprogenitor cells may be used with or without an effective amount of a differentiation agent prior to being used in a neuronal transplant.

In the present invention a preferred aspect of the present invention, embryonic stem cells are grown in standard cellular media (preferably, at least a minimum essential medium, preferably DMEM/F12 or neurobasal media) supplemented with effective amounts of L-glutamine, at least one antibiotic and optionally, one or more of non-essential amino acids, beta-mercaptoethanol, fetal bovine serum, (FBS), knockout serum replacement (KSR), leukaemia inhibition factor (LIF), basic Fibroblast Growth Factor (bFGF), N2 media supplement and B27 cell culture media on a differentiation protein, preferably laminin, in the absence of feeder cells, for a period of at least about 15 days, preferably at least about 17 days or more preferably about 21 days and then isolated. The neuroprogenitor cells so isolated are free from contaminating feeder cells.

Preferred cell media to be used for producing neuroprogenitor cells from embryonic stem cells include the following:

NP-1
DMEM/F12 38.5 ml
KSR-2.5 ml
FBS-7.5 ml
Penstrep 0.5 ml
L-Glutamine 0.5 ml
Non-Essential Amino Acid 0.5 ml
LIF-10 micro-g/ml
bFGF 4 ng/ml of media
Beta mercaptoethanol 0.1 mM NP-2 without bFGF and LIF
DMEM/F12 38.5 ml KSR-2.5 ml
FBS-7.5 ml
Penstrep 0.5 ml
L-Glutamine 0.5 ml
Non Essential Amino Acid 0.5 ml
Beta mercaptoethanol 0.1 mM NP-3 (No Serum)
DMEM/F12
PenStrep
L-Glutamine,
4 ng/ml bFGF
1×N2.

NP-4-Designed for Neuronal proliferation
Neurobasal media
PenStrep,
L-Glutamine
20 ng/ml bFGF
ng/ml LIF
1×B27.

Each of the above cell media may be used alone to produce neuroprogenitor cells for a period of about 9 days, about 15 days, 17 days or 21 days, or alternatively, two or more of the above media may be used for several days within the differentiation period of about 9 days, about 15 days or more (preferably, about 17 days, also preferably about 21 days) to produce neuroprogenitor cells. Examplary preferred treatments using the above-described media include the following:

I: NP-1 (7 days)+NP-3 (7 days)+NP-4 (7 days);
II:NP-2 (7 days)+NP-3 (7 days)+NP-4 (7 days);
III:NP-3 (14 days)+NP-4 (7 days); and
IV:NP-1 (21 days)

Note that in the experiments above as indicated, cells may be exposed to cell media for about 3 to 10 days, preferably about 7 days, about 7 to 17 days, preferably about 14 days and about 14 to 30 days, preferably about 21 days.

In each instance, the embryonic stem cells are grown on a differentiation protein, in this case, preferably laminin (preferably, at 2 micrograms of laminen per cm$^2$ on the tissue culture dish). The preferred time for the treatment is 21 days. All four of the treatments produced neuroprogenitor cells which were free from feeder cells. In the case of treatment II, this allowed the formation of neuronal rosettes on the same plate. Treatment IV utilized a single cell medium (NP-1), above, for the full 21 days. The neuroprogenitor cells produced may be used directly to produce all neural lineages including glia and neurons or continuously propagated in NP-4, above, as adherent cultures without feeder cells.

These neuroprogenitor cultures can then be used directly for differentiation to motor neuron cells, or preferably, these cells are isolated/removed from the cell culture flasks in which the cells were produced and then further differentiated to motor neuron cells using a cell medium comprising effective amounts of FGF2 and optionally, Sonic Hedgehog, retinoic acid and/or LIF. In this method, neuroprogenitor cells are deposited onto differentiation protein (preferably laminin or a laminin containing gel/matrix) grown in cell media containing FGF2 (optionally including Sonic Hedgehog, retinoic acid and/or LIF, but preferably excluding this cofactors to reduce costs) for a period of about 1 to 10 days followed by growing the cells in cell medium without any growth factors for an additional 5 to 20 days. At the end of the second period, the number of motor neurons cells was quite high (usually >90% of the cells in the sample) Unexpectedly, neuroprogenitor cells could be differentiated to motor neuron cells in cellular growth medium in the presence of effective amounts of FGF2, even in the absence of Sonic Hedgehog and/or retinoic acid. This method is advantageous because large quantities of motor neuron cells can be produced in a short (10 to 20 days) period, and relatively little growth factor FGF2 (an expensive component) is used, thus making the present method particularly cost effective.

The following advantages are obtained using the present invention.

1) The process of the present invention relies on simple matrix, lamin, for adherent culture and minimal growth factors (LIF and basic FGF) in a neural basal medium for 10 to 20 days. The resulting neural rosettes which may be preferably produced may be manually passaged and can proliferate as neural progenitors and then differentiate towards post mitotic neurons such as motor neurons. All of this is without any feeder cells or embryoid body or neurosphere transition.

2) The present method produces neuroprogenitor cells with great homogeneity (generally, >90% nestin positive NP cells. These provide more uniform results in cellular assays and differentiation to neuron cells of interest.

3) The processes of the present invention are very cost effective. Since there is no requirement for neural growth factors or inhibitors of the BMP signaling or expensive substrates to grow the cells on, the cost of productions is lower.

4) The yield of cells is generally quite high, since the method does not require embryoid bodies or neurospheres, random differentiation to non-neural type cells is significantly reduced.

5) The cells may be easily used in cell based assays for experimentation. Assays such as immunocytochemistry and several high throughput assays in one step vs. using neurospheres that have to be broken or plated down as is, often in a three dimensional complex structure. These complex structures can confound and complicate many cell based assays using NP cells.

6) The production of motor neuron cells using the present method may start with a more uniform population of neuroprogenitor cells, uncontaminated with feeder cells.

7) Sonic Hedgehog and retinoic acid are not required for differentiation from neuroprogenitor cells of the present invention to motor neuron cells. This represents a huge cost savings in producing motor neuron cells. Moreover, in preferred aspects of the present invention, the FGF2 which is used in a first stage of differentiation of NP to motor neurons, is removed in a second stage differentiation which results in further savings.

8) Using neuroprogenitor cells of the present invention instead of embryonic stem cells, the time required to produce motor neuron cells is reduced by anywhere from 10 to 20 days or more.

9) The neuroprogenitor cells of the present invention may be readily genetically modified, thus reducing the time needed to facilitate the introduction of one or more reporter genes for diseases into the final motor neurons.

The following examples are provided to further illustrate the present invention. It is to be noted here that the examples presented are not to be construed as limiting the invention in any way.

EXAMPLES

Simple and Scalable Method of Producing Primate (Including Human) Neuroprogenitor Cells Methods Cell Culture Rhesus ES cells were routinely cultured in DMEM/F12 base medium (Gibco) supplemented with 20% Knockout Serum Replacement (Gibco), 2 mM L-glutamine (Gibco), 0.1 mM Non-essential Amino Acids (Gibco), 50 units/ml penicillin/50 ug/ml streptomycin (Gibco), 4 ng/ml bFGF (Sigma-Aldrich), and 0.1 mM β-mercaptoethanol (Sigma-Aldrich). Cells were passaged every 3-4 days using 0.05% trypsin-EDTA (Gibco). Cells were cultured on inactivated mouse embryonic fibroblasts (MEFs) plated 3 or more days prior to use.

Neuroprogenitor cells were cultured in DMEM/F12 supplemented with 2 mM L-glutamine, 50 units/ml penicillin/50 ug/ml streptomycin, 20 ng/ml bFGF, and 1×N2 supplement (Gibco). 1×N2 supplement is composed of human transferrin (100 ug/ml), bovine insulin (5 ug/ml), progesterone (6.3 ng/ml), putrescine (16.11 ug/ml), and selenite (5.2 ng/ml). These cells were passaged every 5-7 days by brief (20 seconds) exposure to 0.05% trypsin-EDTA.

Neural Differentiation

Primate ES cells were grown for 0, 3, 7, or 10 days on Matrigel in ES growth medium. Cells were trypsinized and replated on dishes coated with poly-L-ornithine and laminin and grown for 10 days in DMEM/F12 supplemented with 2 mM L-glutamine, 50 units/ml penicillin/50 ug/ml streptomycin, 4 ng/ml bFGF, and 1×N2 supplement. At each timepoint cells were harvested for analysis by flow cytometry.

Neuroprogenitor cells were further differentiated by exposure to DMEM/F12 supplemented with 2 mM L-glutamine, 50 units/ml penicillin/50 ug/ml streptomycin, 4 ng/ml bFGF, and 1×N2 supplement for 7 days. These cells were stained for a panel of neural markers.

Immunocytochemistry

Cells were seeded onto Permanox chamber slides (Nunc) coated with Matrigel or poly-L-ornithine/laminin and fixed with 4% paraformaldehyde/4% sucrose for 20 minutes. Antibodies were directed against SSEA-4 (Chemicon, 1:1000), nestin (Neuromics, 1:100), smooth muscle actin (Dako, 1:50), MAP2abc (Sigma-Aldrich, 1:200), HuC/D (Molecular Probes, 1:50), and Tuj1 (Covance Research Products, 1:500). Antibodies were detected using secondary antibodies conjugated to Alexa Fluor 488 or 594 (Molecular Probes, 1:1000).

Flow Cytometry

Cells were fixed in 2% paraformaldehyde/2% sucrose for 15 minutes, washed twice with DPBS, and held at 4° C. in 1% BSA in DPBS until all samples were collected. For detecting surface markers, cells were blocked in 1% BSA in DPBS and stained with either SSEA-4 (Chemicon, 1:2000) or mouse IgG isotype control (Sigma, 1:2000). Antibody was detected using a fluorescently-conjugated secondary antibody (goat anti-mouse IgG Alexa Fluor 488, 1:1000, Molecular Probes). Cells were analyzed using a Beckman Coulter FC500. 10,000 events were counted.

Real-Time PCR

RNA was collected by resuspending harvested cells in an appropriate amount of RNAlater (Ambion), snap freezing in liquid nitrogen, and storing at −80° C. until use. Total RNA was isolated using the Qiashredder kit (Qiagen) and RNeasy kit (Qiagen) according to the manufacturer's instructions for animal cells. cDNA was generated using the cDNA Archive Kit (Applied Biosystems). cDNA was mixed with 2×Taqman Universal PCR Master Mix (Applied Biosystems) and applied to a custom Microfluidics Card (Applied Biosystems) containing 96 human-specific Taqman primer/probe sets for pluripotency genes and genes specific for ectoderm, mesoderm, endoderm, or trophectoderm. Analysis was conducted using SDS 2.1 software.

Statistical Analysis

Figure 2:
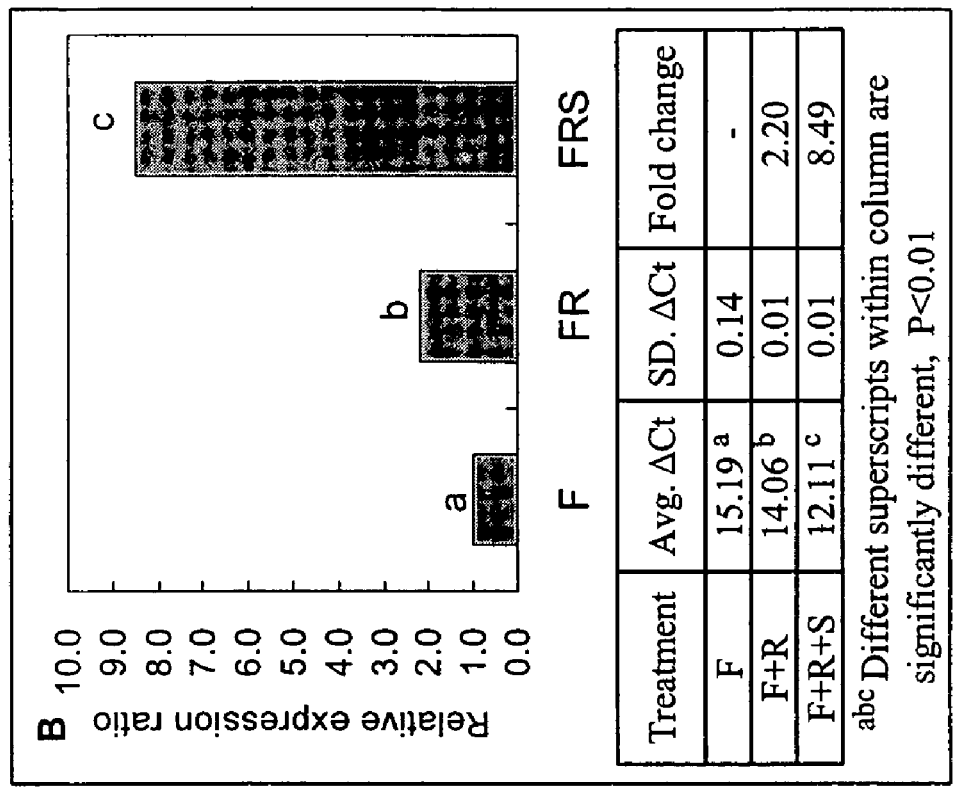
FIG. 2 shows (A-B) Gene expression fold change by signaling molecules bFGF (F), retinoic acid (R), sonic hedgehog (S) using real time RT PCR: (A) OLIG2 expression change, (B) HLBX9 expression.
Figure 2:
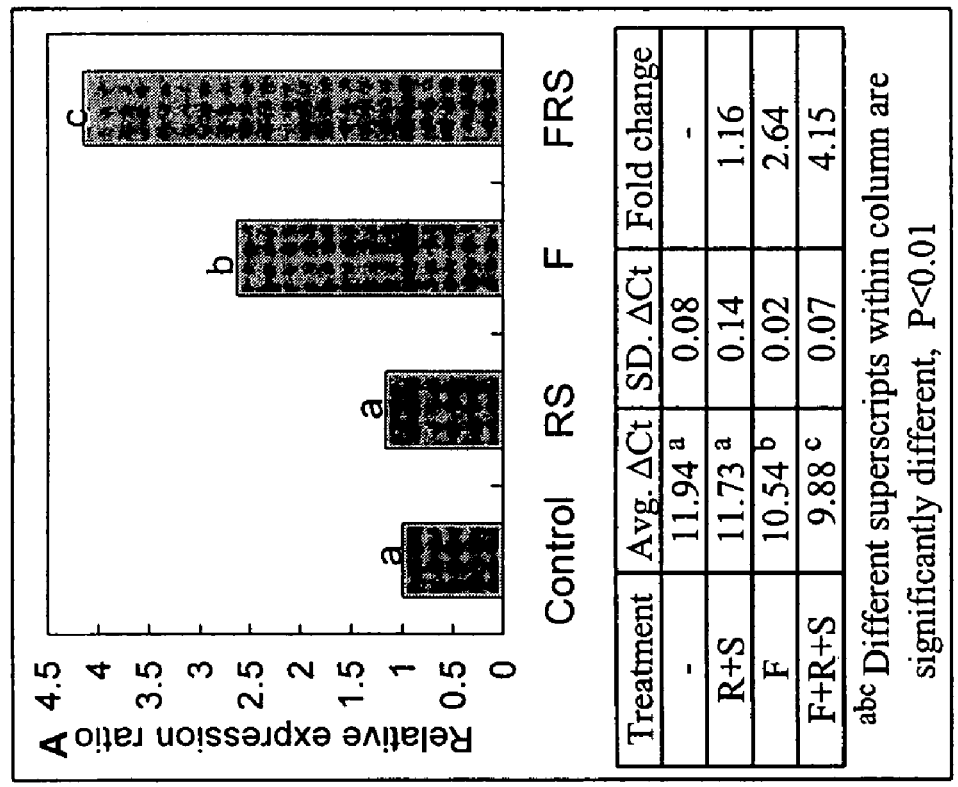

After excluding failed reactions (reactions called as 'undetermined' by the SDS software) and genes for which fewer than 2 replicates existed from further analysis, ΔCt values were calculated using 18s RNA as an endogenous control/normalizer. For each gene, the mean ΔCt value and standard deviation were calculated using all available replicates. Significance was determined by running t-tests for each gene at a 95% confidence interval between d0/d7, d0/d17, and d7/d17. Values greater than 0 were called significant. ΔΔCt values were calculated for each gene at timepoints d7 and d17, using d0 as the calibrator. These values were then subjected to the formula $2^{-\Delta\Delta Ct}$ to yield the mean fold change for each gene at both timepoints. Results are expressed as the mean fold change±SD. For FIG. 2, results are expressed as average $\log_{10}$ fold change±SD. For this figure ΔCt and fold change values were calculated within each replicate, subjected to the log function, and then averaged in order to produce relevant SD values.

Results

Differentiation of Primate ES Cells to Neuroprogenitor Cells

In order to generate an adherent population of neural progenitors, we took a two step approach. Primate ES cells were plated on Matrigel in 20% KSR medium and allowed to spontaneously differentiate for 7 days. The cells were briefly exposed to trypsin and replated on a polyornithine/laminin substrate in a serum free medium containing N2 supplement and 4 ng/ml bFGF. To determine the percentage of cells that were differentiating in response to the treatment, we collected cells at 3 timepoints and subjected them to flow cytometry. There was a decrease in expression of SSEA-4, a cell surface glycolipid and marker of pluripotency, as the ES cells moved toward a neural phenotype. After 10 days in culture on polyornithine/laminin these cells had developed a distinctive neural progenitor morphology. Immunocytochemistry revealed these cells to be nestin positive and SSEA-4 negative.

Characterization of Neuroprogenitors using Real Time PCR

To further characterize the populations of cells found during this differentiation process, cells were harvested for real time PCR at d0, d7, and d17. These three samples were assayed for the expression of a panel of 96 genes. Genes whose expression met specific criteria (see Methods) were placed into the following groups: a) significant fold change with SD<1, b) significant fold change with SD>1, c) no significant fold change. Genes with no significant fold change included β-Actin, cyclin A2, and NEDD4. The remaining genes in this group had widely variable standard deviations and were not included for further analysis. Genes with a significant fold change but standard deviations greater than 1 were likewise not considered for further analysis. Table 2 summarizes genes with a significant fold change at either day 7 or day 17 and a SD<1.

Culture of Neuro Progenitors

After their derivation, the cells were passaged enzymatically every 5-7 days with >95% viability. The cells were frozen at p2 in serum-free freezing medium with 10% DMSO and successfully recovered. The cells retained the same morphology after 3 passages as they had after derivation.

Differentiation of Neural Progenitors to Mature Neurons

In order to assess the ability of these cells to differentiate to mature neurons, the neural progenitors were grown for seven days in a serum free medium containing a low concentration of bFGF. The cells were stained for Tuj1, Hu, and MAP2, all markers of post-mitotic neurons. Both MAP2 and Tuj1 staining localized cytoplasmically in cell bodies and neurites, while Hu staining was confined to the nucleus.

Neuroprogenitors from Feeder-free Human Embryonic Stem Cell Culture

Methods

Human ES cells (BG02) were grown on laminin, approximately 2 microgram laminin per cm square as recommended by Sigma is used to coated 24 well tissue culture dishes. There were four different treatments each with 6 replications. Each treatment was followed for 21 days. Three wells from each treatment were harvested for gene expression studies and remaining wells were used for neuronal specific immunostaining.

The Treatments are
I: NP-1 (7 days)+NP-3 (Days)+NP-4 (7 days)
II:NP-2 (7 days)+NP-3 (7 Days)+NP-4 (7 Days)
III:NP-3 (14 Days)+NP-4 (7 days)
IV:NP-1 (21 days)

NP-1
DMEM/F12 38.5 ml
KSR-2.5 ml
FBS-7.5 ml
Penstrep 0.5 ml
L-Glutamine 0.5 ml
Non Essential Amino Acid 0.5 ml
LIF-10 micro-g/ml
bFGF 4 ng/ml of media
Beta mercaptoethanol 0.1 mM NP-2 without bFGF and LIF
DMEM/F12 38.5 ml
KSR-2.5 ml
FBS-7.5 ml
Penstrep 0.5 ml
L-Glutamine 0.5 ml
Non Essential Amino Acid 0.5 ml
Beta mercaptoethanol 0.1 mM NP-3 (No Serum)
DMEM/F12
PenStrep
L-Glutamine,
4 ng/ml bFGF
1×N2.

NP-4-Designed for Neuronal Proliferation
Neurobasal media
PenStrep,
L-Glutamine
20 ng/ml bFGF
10 ng/ml LIF
1×B27.

All three treatments worked to some extent, but treatment II, above allowed the derivation of neuroprogenitor cells in the form of neuronal rosettes on the same plate. Also, we showed that the derived neuroprogenitor cells have similar properties in terms of culture morphology and marker gene expression.

The differences between this HESC example and the method used in the primate derivation above are not major and they will both work on both types of ESC but we did a few things different recently wit the HESC to save time and money.

1) Primate ES cells were initially grown on Matrigel before culturing on Laminin-Ornithine. Whereas, here we directly grew human ESC on Laminin (not with polyomithine and no matrigel). The polyomithine and matrigel procedure can be substituted but straight laminin is easier and less expensive. The laminin alone approach worked quite well.

2) In the above primate example, the length of time used with ES media is 7 days and on neuronal permissive media is 10 days. In the above-described hESC protocol, the total regime of treatment is most preferably 21 days, although 15 days, more preferably 17-18 days should be sufficient and enough to see the neuronal rosettes with this method too. In the preferred method, it is three different media are used (NP-2, NP-3 and NP-4) for 7 days each.

3) For primates, we described a media called neuronal permissive media. It is pretty much the same as NP-3 above, except in the case of the primate the media contains high bFGF (20 ng/ml). In the present example, the high amount of bFGF was used in NP-4 for 7 days.

4) The main difference from the above primate example is that, once the cells were plated here for hESC we do not need to passage, which was not the case for primate protocol. In that case, passaging of cells was done from Matrigel to Laminin-Ornithine. This saves time and money.

In the example described above, we have developed a process for deriving adherent human neuroprogenitor cells without feeder layers, an important result. This is important because it eliminates the potential of contamination of feeder cells such as mouse feeder cells during the isolation of the neuroprogenitor cells. This method also eliminated the inefficient and time consuming step of isolating and passaging the neuroprogenitor cells off of the feeder cells or another matrix like matrigel.

EXAMPLE

Human Motor Neuron Differentiation Using Human Embryonic Stem Cells

Method

NIH approved HESC (BG01) were first committed to a neuroprogenitor cells (als, neuro epithelial cell (NEP) phenotype (FIG. 1A). These cells are self-renewing and can give rise to all the cells that comprise the mammalian central nervous system, including various types of neurons and glial cells. See, Zhang, et al., *Nat. Biotechnol.*, 19(12), 1129-33 (2001). We have cultured NEP for 10 months in neurobasal medium supplemented with B27 (1×), LIF (10 ng/ml) and bFGF (20 ng/ml) in serum free medium without overt changes in expression of Nestin, Musashil or SOX 1, 2, and 3, or in differentiation potential to neuron and glial phenotypes. Importantly, these cultured adherent human NEP cells lose expression of OCT4 (FIG. 1B, 1C). Retinoic acid (RA) and sonic hedgehog (Shh) are well known molecules involved in motor neuron differentiation. When mouse embryonic stem cells were induced to neural fate and exposed to Shh and RA, the differentiating population was preferentially directed to motor neuron fate (Islet 1, HB9 and Tuj1 positive). Wichterle, et al., *Cell,* 110(3), 385-387 (2002). In addition, basic fibroblast growth factor (bFGF) alone, induced long-term cultured fetal human neural stem cells to form cholinergic neurons (see Wu, et al., *Nat. Neurosci.,* 5(12), 1271-78 (2002)), suggesting that bFGF may also be an effective growth factor for in vitro differentiation to human motor neurons. Thus, it was postulated that subjecting adherent human NEP cultures to these three factors might lead to relatively high proportions of motor neuron phenotypes.

First, we examined gene expression of PTCH, the Shh receptor, to determine whether this portion of the Shh signaling pathway was present in our propagating NEP. Gailani and Bale showed that the vertebrate homolog of Drosophila PTCH is expressed in all known target tissues of Shh and that expression of this receptor can be a useful biological marker in screening tissue for Shh treatment. Gailani and Bale, *J. Natr. Cancer Inst.,* 89(15), 1103-09 (1997). We found PTCH gene expression in cultured NEP; however, PTCH expression alone does not necessarily represent responsiveness to Shh for motor neuron cell specification, which must be determined by examining the effect of Shh and other factors on motor neuron lineage gene expression and induced phenotype.

The motor neuron progenitor gene, OLIG2, is expressed early in motor neuron induction. Novitch, et al., *Neuron,* 31(5), 773-89 (2001). Using real time RT-PCR, we found that bFGF significantly increased OLIG2 expression, and when bFGF was combined with RA and Shh, OLIG2 expression was further increased (FIG. 2A). However, the combination of Shh and RA alone had little effect on OLIG2 expression, suggesting a critical role for bFGF in motor neuron induction. Subsequently, we examined expression of the motor neuron gene HLBX9 to investigate the effect of Shh and RA on motor neuron differentiation. Based on the OLIG2 results, bFGF was included at the time of RA or RA plus Shh exposure. The combination of RA and bFGF produced a 2·20 fold increased in HLBX9 expression level, and combining bFGF, Shh and RA increased HLBX9 expression 8·49 fold higher than bFGF alone in human NEP (FIG. 2B).

In addition to motor neuron-related gene expression, motor neuron phenotype markers were examined. NEP differentiated to motor neurons that expressed Islet 1, Tuj1 (FIG. 1E) and ChAT (FIG. 1D). Based on this criterion, approximately 20 to 30% of the cultures have a motor neuron phenotype when they are exposed to neural basal medium supplemented with B27 (1×), bFGF (20 ng/ml), Shh (1 ug/ml) and RA (2 uM) for 7 days and then 14 additional days without these growth factors on polyomithine and laminin coated slides. With our current culture conditions, NEP proliferating adherently in bFGF-containing medium gave rise to motor neurons even without Shh and RA exposure. Although the underlying mechanisms remain to be defined, our propagating NEP may have been primed to differentiate toward a motor neuron phenotype as a result of low level exposure to bFGF during NEP proliferation. This growth factor has previously been shown to induce cholinergic neuron differentiation in fetal neural stem cells. Wu, et al., supra.

In this example, we present the motor neuron differentiation from hESC-derived NEP and the effects of extrinsic factors on motor neuron induction of the NEP. We demonstrated that motor neuron induction was affected not only by the kinds of factors applied, but how they were combined, and that bFGF, Shh and RA had additive and synergistic effects. We also showed that an established NEP culture system can serve as an in vitro model for the study of human motor neuron development. The study of derived motor neurons will expedite the elucidation of molecular mechanisms that regulate survival of motor neurons and also can serve as a model system for screening for motor neuron disease and spinal cord injury treatments.

Long Term Proliferation of Human Embryonic Stem Cell-Derived Neuroprogenitor Cells Using Defined Adherent Culture Conditions After human embryonic stem (ES) cells were established, there was an immediate interest in differentiating these pluripotent cell lines toward a neuronal cell fate as a promising source for replacement cell therapy. To that end, the following experiments were conducted.

A variety of methods have been used to derive NEP from ES cells. See, Zhang, et al., *Nat Biotechnol.,* 9(12):1129-1133 (2001); Reubinoff, et al., *Nat Biotechnol.* 19(12):1134-1140 (2001); and Calhoun, et al., *Biochem Biophys Res Commun.,* 306(1):191-197 (2003). However, most of these methods have used cell aggregation or embryoid bodies (EBs), which allows stochastic differentiation into all three germ layers, including NEP.

In this study, factors required for the neural differentiation of human ES cells were examined and conditions allowing further proliferation were optimized. We show that adherent cultures of human ES cells in serum-deprived medium without feeder layers gave rise to a rosette enriched population. Characterization of this population showed that the cells were multipotent NEP with proper phenotype marker profiles and that they were able to differentiate further to both A2B5-positive and PSNCAM-positive precursor cells. Thus, this study demonstrates that derived NEP can be cultured more than six months in optimized conditions without the cells losing their capacity for neural and glial differentiation while maintaining a stable karyotype.

Methods

Human ES Cell culture. Human ES cell lines of BG01 and BG02 used in this experiment were cultured on mouse embryonic fibroblasts (MEF) layer, inactivated by mitomycin C. Mitalipova, et al., *Stem Cells,* 21(5):521-526 (2003). Since there were no differences in experimental results due to ES cell lines in this study, data from both cell lines were pooled. The cells were cultured in ES medium of DMEM/F12 medium (Gibco) supplemented with 15% serum and 5% knock-out serum replacement (KSR, Gibco), 2 mM L-glutamine, 0.1 mM MEM non-essential amino acids, 50 U/ml penicillin, 50 ug/ml streptomycin, 4 ng/mL basic fibroblast growth factor (bFGF, Sigma) and 10 ng/mL Leukemia Inhibitory Factor (LIF, Chemicon). For passage, ideal colonies were mechanically dissected into small pieces and replated on mitotically inactivated MEF and the medium changed every other day as described (19). These cell lines have maintained their distinct stem cell morphology and karyotype and remain Oct-4- and SSEA4-positive. Rosler, et al., *Dev. Dyn.,* 229(2): p. 259-74, 2004.

Antibodies and immunocytochemistry. Cells plated on polyomithine/laminin coated permanox slides were washed in PBS and fixed with 4% paraformaldehyde/4% sucrose in phosphate buffered saline (PBS) for 15 min. Fixed cells were washed two times with PBS before staining. Permeabilization and blocking was carried out in blocking buffer consisting of 0.1% Triton, 3% goat serum in Tris buffer for 40 min. For cell surface antigen, permeabilization was excluded. Primary antibodies were applied in blocking buffer for 2 h at room temperature (RT) and washed three times in blocking buffer before secondary antibody application. Secondary antibodies of goat anti-mouse Alexa-conjugated, goat anti-rabbit Alexa-conjugated (Molecular Probe) were diluted at 1:1000 in blocking buffer and applied to cells for 40 min at RT. After two washes in PBS, DAPI was applied for nuclear staining for 10 min, and cells were observed under the fluorescence microscope. For flow cytometry application, cells were harvested by trypsinization and suspended in PBS to be fixed and stained using the same procedure coupled with serial centrifugation at 3000 rpm and resuspension in PBS. For negative controls, first antibodies were omitted and the same staining procedure was followed. Primary antibodies and dilutions used included the following: mouse anti-Nestin (1:100; R&D system), rabbit anti-Nestin (1:200; Chemicon), rabbit anti-Musashi 1 (1:500; Chemicon), mouse anti-beta III tubulin (1:400; Sigma), rabbit anti-Tuj (1:500; Covance), mouse anti-Hu (1:50; Molecular Probes), mouse anti-muscle actin (1:50; DAKO), mouse anti-a feto protein (1:50; DAKO), rabbit anti-GFAP(1:50; Sigma), mouse anti-O4 (1:10; Chemicon), mouse anti-PSNCAM (1:400; Abcys), mouse anti-A2B5(1:100; a gift from Mayor Proschel).

Experimental design

All experiments were replicated three times unless otherwise noted.

The effect of ES, DN2 and MEDII media on differentiation of stage 1 ES cells cultured with feeder cells. After manual passage onto fresh feeder cells, hES cells were allowed to proliferate in ES medium for seven days (stage 1). Cell differentiation was then induced with either DN2 or ES medium for another seven days (stage 2). DN2 medium is DMEM/F12-based medium supplemented with N2 (Gibco), L-glutamine, penicillin/streptomycin(P/S) and 4 ng/ml bFGF. To understand and follow the differentiation steps applied here, phenotype marker expression was examined at various time intervals. At stages 1, 2 and 3, populations were harvested and the markers Musashi-1, Oct-4 and Nestin, an early NEP stem cell marker, were observed. Immunocytochemical analysis was also performed on the adherent cell population. The cells at both stages were double-stained with Nestin and Oct-4 and observed under the fluorescence microscope for immunocytochemical examination associated with morphology. Groups that displayed phenotypic difference were then subjected to quantitative analysis for these same markers using flow cytometry.

The effect of ES and DN2 media on differentiation of stage 2 ES cells in adherent cell culture without feeder cells. To improve NEP cell derivation, a method using adherent differentiation was exploited. It was possible to isolate subpopulations of stage 2 cells that had infiltrated under the feeder layer to attach firmly on culture plates. To test the effect of ES and DN2 media on this derivation method, the mouse feeder layer was physically removed from each group of stage 2 cells in calcium/magnesium-free PBS. The remained cells were cultured another three days in respective media. At stage 3, populations were harvested from each group, and morphology and phenotype marker expression of Oct-4, Nestin and Musashi 1 was observed as described in experiment 1 using flow cytometry and immunocytochemistry for Oct-4, Nestin and Musashi-1.

Characterization and examination of differentiation capacity of derived NEP-like cells. Rosette-forming populations of stage 3 NEP cells derived in DN2 media from experiment 2 and rosette-forming NEP populations from experiment 3 were characterized by immunocytochemistry to examine the phenotype of NEP using the phenotype markers Nestin, Musashi 1, Oct-4, muscle actin and a-fetoprotein. For terminal differentiation, NEP-like cells were cultured in neurobasal medium (Gibco) and supplemented with B27 (Gibco), L-glutamine and penicillin/streptomycin without b-FGF for 14 days. For oligodendrocyte differentiation, NEP-like cells were exposed to 5 ug/ml PDGF (Upstate) and 50 uM 3T3 (Sigma) for 6 days before terminal differentiation. Differentiated cells were characterized using the Effect of culture medium. To obtain a more uniform subculture system, two different kinds of base media—DMEM/F12 (D) and neurobasal medium (N)—were tested with supplements of either N2 or B27. Stage 3 NEP-like cells were allocated into four different media: DN2, NN2 (neurobasal medium supplemented with N2), NB27 (neurobasal medium supplemented with B27), as described above with the same supplement of L-glutamine, P/S and 4 ng/ml bFGF. After 12 days of culture, cells were harvested and examined for morphology and viability using the Guava ViaCount (Guava Technologies) flow cytometry assay. Briefly, the Guava ViaCount reagent combines two different DNA dyes. One dye binds to the nucleus of every cell to give a total cell number and the other dye binds differentially to only non-viable cells. The data collected include total cell number and viability of the sample.

Subculture of NEP cells. NEP derived from DN2 were further propagated in NB27 with L-glutamine, P/S, 10 ng/ml LIF and 20 ng/ml bFGF on poly-ornithine and laminin coated dishes. Cells were continuously passaged by either by mechanical trituration or by trypsin ($1 \times 10^5/cm^2$) to be replated. After more than 6 months in culture, NEP-like cells were characterized as described before (Exp.4) and karyotyped using standard karyotype protocols, and chromosomes were counted. Briefly, cells were treated with 0.02 µg/µl colcemide for 1.5 hours and harvested to be hydrated and fixed. Chromosomes were stained with Giemsa and then counted (15 cells).

Effect of LIF and bFGF on subcultured NEP cells. Two groups of cultured NEP cells, one less than 1 month (<1 mo) and the other approximately 6 months (6 mo) in NB27 (described in previous section), were dissociated by 0.05% trypsin to obtain a single-cell suspension, and 50,000 cells/$cm^2$ were plated in one of the subculture media on polyomithine and laminin-coated dishes. Two concentrations of two growth factors (LIF; 0 or 10 ng/ml and bFGF; 0 or 20 ng/ml) in NB27, were applied to cells. Cells were harvested from each group and nuclei were counted by flow cytometry on days 1 and 14. Plating efficiency rate was calculated as the ratio of cells harvested to cells plated on day 1. Proliferation was measured on day 14. For each replicate, counted nuclei from the four treatment groups were added to obtain an overall total. The total cell number within each group was then divided by the overall total cell number and expressed as a percent. This data conversion was carried out to reduce biological variation due to replicate preparation.

Effect of oxygen concentration on subcultured NEP cells. To examine the effect of oxygen concentration on cell proliferation and viability, the subcultured NEP cells (described above) were dissociated by 0.05% trypsin, and $2 \times 10^5$ cells/$cm^2$ were plated and propagated using the NEP subculture process, except one group was cultured at oxygen concentration of 20% and the other group was cultured at 5% O2. After 7 days of culture, cells were harvested to calculate total cell number and viable cell number, as described previously.

Statistical analysis. For each parameter, significance of main effects was determined using the GLM procedure of SAS 8.01. Significance of differences among individual treatment means was determined by the least square means method. Differences were considered significant at P<0.05.

Results

Experiment. The effect of ES and DN2 media on differentiation of stage 2 ES cells in adherent cell culture without feeder cells. We found differences for stage 3 cells cultured in ES medium compared to cells cultured in DN2 media after feeder cell removal. Following feeder cell removal, cell culture gave rise to enriched rosette formation in DN2 media, characteristic of NEP cell formation, but ES medium-derived cell culture resulted in cells with large nucleus to cytoplasmic ratios, characteristic of ES cells. DN2 groups developed a similar differentiation pattern with distinct structure of neural tube-like formation and further rosette-enriched populations.

Experiment. Characterization and examination of differentiation capacity of derived NEP-like cells. Rosette forming NEP-like cells were obtained from DN2 derived stage 3 cells. Nearly 100% of rosette forming cells were positive for the early NEP markers Nestin and Musashi 1 and negative for later stages of differentiation markers A2B5, PSNCAM, Hu, GFAP, O4.

Removal of FGF and LIF from the culture medium resulted in further differentiation of NEP cells to form intermediate precursors staining positive for A2B5 or PSNCAM. After 14 days of culture in neurobasal medium supplemented with B27 without bFGF, terminally-differentiated cell cultures contained neurons positive for Hu and Tuj, astrocytes stained with GFAP and Dapi and oligodendrocyte stained with O4.

Experiment. The Effect of Medium, Supplement, Growth Factor and Oxygen Conditions on Proliferation and Viability of Subcultures of Derived NEP-Like Cells. Effect of Culture Medium.

The effects of base media and supplements on cell survival were determined in this experiment. A higher percent of cells cultured in NN2 survived compared to cells cultured in DN2 (33.8% DN2 vs 75.4% NN2 P<0.05), indicating that derived NEP cells survived better in neurobasal medium than DMEM medium with N2 supplement. Furthermore, the groups of NN2 and DN2 supplemented cultures developed rosette structures. Also, the addition of DN2 medium increased cell survival rate from 33.8% to 77.6% (p<0.05). In contrast, there was no difference in survival rate or the morphology of cells between N2 and B27 supplement when added to the neurobasal medium.

Subculture of NEP cells. These derived NEP cells have been cultured for more than 6 months without losing this characteristic and maintained a normal karyotype. Cells retained expression of Nestin and Musashi-1, and when terminally differentiated in medium lacking bFGF and LIF, the cell population included both neurons and glial cells (data not shown). When NEP cells were karyotyped with Giemsa staining, all 15 samples examined were stable with 46 XY chromosome numbers.

Effect of LIF and bFGF. NEP cells propagated in NB27 for approximately one month or 6 months were subjected to different concentrations of LIF and bFGF and cell survival was determine as well as cell proliferation over 14 days. For early NEP cells (1 mo) the addition of LIF, bFGF or LIF+ bFGF had no effect on plating efficiency and was only about 50%, indicating a relatively high rate of cell death. In contrast, the presence of bFGF increased cell proliferation more than four-fold (8.9% vs. 38.5% p<0.05), while LIF had no effect on proliferation of NEP cells either in the presence or absence of bFGF. After 6 months in LIF supplemented culture, LIF, bFGF and the combined groups exhibited a higher plating efficiency than the control. bFGF had a greater effect on cell proliferation than LIF (p<0.05) for both the short-term (<1 mo) and long-term (6 mo) NEP cultures, However, only long term cultured NEP cells demonstrated increased proliferation rate for both LIF and bFGF individually and in combination.

Effect of oxygen concentration. After 7 days of culture in NB27 medium, total NEP-like cell number was approximately 25% greater in 5% oxygen compared to 20% oxygen (p<0.05). Considering that the plating efficiency was 50% when NEP-like cells were dissociated, we estimated that there was approximately a 2.5-fold increase in cell proliferation for 5% oxygen and a 1.96-fold increase for 20% oxygen.

Discussion

The overall objective of these experiments was to obtain efficient neural differentiation of hES cells and to develop a defined medium that would be supportive of NEP stem cells and allow enzymatic passage, thereby facilitating more controlled and refined future studies. In contrast to previous reports, we employed both immunocytochemistry and flow cytometry analysis in order to obtain both quantitative and morphological information on NEP formation at various stages of in vitro differentiation and culture conditions. Immunocytochemistry makes it possible to identify specific markers on cells; however, quantification is difficult and often subjective, and sample preparation can add bias due to selection from limited cell populations. The benefit of immunocytochemistry is that it allows co-localization of markers with the associated cell morphology, while flow cytometry analysis provides more objective quantification for marker expression.

The majority of studies investigating mouse and human ES cell differentiation to neural progenitors have used methods involving cell aggregation or embryoid body (EB) formation. EB formation in serum-containing medium included cells differentiated into NEP, see Zhang, et al., supra and Rathjen, et al., supra but also led to stochastic differentiation yielding multiple cell lineages, thus limiting the overall yield of the desired NEP cells (Dang, et al., *Biotechnol Bioeng.* 78(4): 442-453,2002) compared EB differentiation cultures to adherent differentiation culture and reported that cell number limitation was not a factor in adherent differentiation cultures. In addition, they showed that adherent differentiation seemed to exclude cell differentiation toward hematopoietic development. Ying et al used adherent differentiation with mouse ES cells and obtained efficient neural commitment (see, *Nat Biotechnol.*, 21(2):183-186, 2003). In our study, hES cells were allowed to differentiate adherently in serum free medium, and we were able to obtain efficient neural differentiation. Subpopulations of stage 2 cells infiltrated underneath the feeder cell layer to attach firmly on culture plates. Serum deprivation apparently is crucial for ectodermal derivation and removal of feeder cell layer produced homogenous rosette formation from homogenous spread of cells in adherent culture conditions.

In an attempt to follow the spatial and temporal differentiation of ES cells to neural lineages we divided the process into three stages. We found that Oct-4 expression gradually decreased with the onset of expression of the NEP cell markers Nestin and Musashi-1. At an initial stage (stage 1), when cells were allowed to proliferate in ES medium, the majority of cells were positive for both pluripotent and NEP cell markers. Further differentiation resulted in morphological changes, including neural tube-like structures, when cells were cultured in DN2 supplemented media but not in ES medium. Visual inspection indicated that in the DN2 group, cell populations developed rosette-like structures in over 70% of the total culture area, and there was little difference in rosette numbers or appearance between these two groups. The neural tube-like structures and rosettes have been previously identified as characteristic morphology of NEP.

We found that removal of LIF, nonessential amino acids, KSR and undefined factors in serum forced ES cells to choose a neurectodermal fate. Rosette formation was not promoted when cells were cultured in ES medium with these factors included. Instead, cells retained their Oct-4 expression and delayed progression to a more differentiated state. This finding is similar to that seen with spontaneous differentiation. For example, Reubinoff et al, supra showed that over four weeks of culture was required for ES cells to differentiate into NEP-like cells, and their system also resulted in endodermal and mesodermal differentiation.

When tube structure-forming cells were dissociated and passed in DN2, more than 98% of cells died and failed to form NEP cell colonies. This finding is similar to results obtained with mouse cells. The inclusion of supplement with LIF can improve this process. Using just morphological analysis, when cells were not disaggregated and their cell to cell contact remained, a more uniform and enriched rosette formation was obtained after another three to four days of culture in DN2 than cells passaged as single cells. Rosette enriched stage 3 from DN2 groups and colonies developed from dissociated stage 2 cells were characterized to determine phenotype markers, and further differentiation capacity was examined to determine whether these cells correspond to NEP. NEP is designated as an unrestricted neural stem cell population based on Nestin expression, and these cells are non-immunoreactive to any restriction markers such as A2B5 and PSNCAM. Our results showed that the derived NEP-like cells had the same phenotype profile as rodent NEP or human NEP purified from fetal tissue. They were not immunoreactive to restriction markers or to specific differentiation cell markers of neurons or glial cells, but they were immunoreactive to Nestin and Musashi-1. In addition, the rosette enriched population was not immunoreactive to Oct-4 or mesodermal or endodermal markers. Mayer-Proschel showed that neural cells derived from fetal tissue were heterogeneous, with 50% of the population expressing A2B5. Another step of immunopanning was required in order to obtain an enriched NEP population. In our study, enriched NEP cell populations were obtained through an efficient differentiation protocol. As differentiation progressed, cells expressing precursor markers of PSNCAM or A2B5 appeared As set forth above, experiments were conducted to further define medium requirements that would support NEP cells and allow enzymatic passage and long term culture of these cells. We tested two base media, DMEM/F12, which has been used for various cell cultures including somatic cell lines and ES cell culture, and neurobasal medium, which was formulated for long term culture of rat hippocampal neurons. We also tested two supplements: N2 and B27. N2 is a well-known commercially available chemically defined concentrate developed to support growth of neural cell lines and includes insulin, transferrin, progesterone, putrescine and selenite. B27, also commercially available, is an optimized serum substitute for low density plating and growth of CNS neurons. We found that the serum free base medium DN2 did not support these NEP-like cells. In this medium cells lifted off the plate around day 7 of subculture and were trypan blue positive. In this study, comparison of DMEM/F12 and neurobasal medium showed that neurobasal medium supported NEP stem cell culture when supplemented either with N2 or B27. It also supported the survival of dissociated cells and allowed them to proliferate. Therefore, neurobasal medium supplemented with B27 was chosen as proliferation medium and further experiments were conducted using NEP cells cultured in this medium. This medium has been shown in previous studies to support survival and expansion of both adult neural stem cells and fetal and postnatal brainstem neurons in vitro.

We also tested the effects of the growth factors LIF and bFGF on subculture of NEP-like cells. Mouse neural stem cells have been shown to be dependent on bFGF, and it was critical for neurosphere formation. The presence of LIF also supports and increases neurosphere formation; however, whether it acts by inducing differentiation of ES cells or by enhancing proliferation is not clear. In fetus-derived human neural stem cells, supplementing with both hLIF and bFGF enhanced proliferation rate. In our study done with short term cultured NEP (<1 mo), bFGF appeared to promote cell proliferation but supplement with LIF had little effect, nor was there a synergistic effect when LIF was combined with bFGF. Zhang, et al., supra, reported that LIF had no effect on proliferation of derived NEP after 14 days culture. However, we found that after six months culture in LIF-containing medium increased cell responsiveness and cell proliferation was improved.

Physiological oxygen concentration does not exceed 5%; however, in conventional cell culture, oxygen concentration is maintained at 20%. In rat CNS stem cell culture, it has been reported that reduced oxygen concentration helped to improve cell proliferation and to reduce apoptosis. We tested whether reduced oxygen concentration produces the same advantage on the growth of NEP-like cells derived from human ES cells. In agreement with this previous study, low oxygen concentration improved cell proliferation rates approximately 25% after one week of culture. Because there was no difference in viability as measured by flow cytometry, the increased cell numbers do not appear to be due to increased initial cell survival.

CONCLUSION

In this study, we showed that NEP cells can be derived from human ES cells efficiently by adherent differentiation in defined medium. Derived NEP was broadly characterized with phenotype markers and phenotype profile; in addition, differentiation capacity was similar to that of in vivo purified human NEP. Further NEP subculture conditions were optimized and cells were propagated successfully for over 6 months without loss of differentiation potential or stable karyotype. Our efficient derivation and proliferation of NEP demonstrates that this system can serve as an in vitro model for the examination of human neural development. A defined culture system would be ideal for further studies of effects of extrinsic factors on neuronal cell fate decision. In addition, long term cultured NEP may be good candidates for replacement cell therapy with little possibility of pluripotent cell contamination.

Derivation and Proliferation of Neuroepithelial Stem Cells from Human ES Cells

The main focus of this study was to establish neuroprogenitor from human ES cells. Accordingly, we examined the factors affecting derivation and further proliferation of neuroepithelial (NEP) stem cells from human ES cells. ES cells cultured in defined medium, developed a distinct canal structure which could be isolated by two methods, dissociation and adherent separation by physical feeder removal. Dissociated cells formed colonies comprised of cells characterized as NEP. Further characterization indicates that these cells expressed markers associated with the earliest multipotent neural stem cells and can thus be characterized as NEP. A majority of the cells were positive for Nestin, a neural intermediate filament protein, and Musashi-1, a neural RNA binding protein, while few cells expressed further differentiation markers such as PSNCAM, A2B5, MAPII, GFAP, and 04. Further differentiation of these putative NEP cells over eight days gave rise to a mixed population of progenitors that included A2B5 positive and PSNCAM positive cells. When fully differentiated, cell populations contained postmitotic neurons, astrocytes and oligodendrocytes. Neurobasal medium supplemented with B27, bFGF and LIF at low oxygen conditions was identified as an ideal culture setting to proliferate and culture the NEP. Cells have been proliferated successfully in this condition for over six months without losing their multipotent neural stem cell characteristics and maintenance of stable karyotype.

Motor Neuron Differentiation of Neuroepithelial Stem Cells by Inductive Signaling Molecules After successful derivation and proliferation of NEP, we next studied their differentiation into specific types of neurons. To differentiate NEP into motor neurons, specific morphogens that have been demonstrated as important in development were introduced to short and long term cultured NEPs. These included sonic hedgehog (Shh), retinoic acid (RA) and basic fibroblast growth factor (bFGF). First, freshly isolated (less than one month, early) and propagated (greater than three months, late) cultures of NEPs were characterized by examination of candidate genes expressed in the developing CNS. Both groups expressed the genes Sox1, Sox2 and Sox3 in addition to the Shh receptor Patched 1 (PTCH). Furthermore, both were able to generate cells with motor neuron phenotype when spontaneously differentiated. Therefore, both populations were exposed to inductive signals for the stimulation into motor neurons. It was shown that bFGF was required for induction of Shh and RA mediated increases in the motor neuron progenitor gene OLIG2 expression using late NEP. Subsequently, the RA and Shh role in motor neuron derivation was shown by examining motor neuron gene of HLXB9 (HB9) expression in early and late NEPs. Increased HB9 expression was shown in both early and late NEPs by RA. However, they differed in their responses when combined with Shh. Expression changes of the motor neuron gene HB9 in response to Shh combined with RA was greater in early NEP than in late NEP. In addition, downstream target gene over-expression was shown only in early NEP, whereas there was no change in late NEP. This study suggests that NEP derived from HESC can form a motor neuron phenotype and that Shh, bFGF and RA can differentially affect expression of motor neuron associated genes in the NEP.

High throughput using NP for Drug Discovery and Neurotoxicity

In neurodegenerative disease such as Spinal Muscular Atrophy (SMA), Amyotrophic Lateral Sclerosis (ALS), Multiple Sclerosis, Parkinson's disease, and Alzheimer's, specialized cells known as neurons have become irrevocably damaged and cannot function properly. Unfortunately, the biomedical research needed to develop new drugs and methods for repair or replacement of damaged neurons is severely hampered by the lack of an adequate in vitro human neuron cell-based model.

Ion channels are involved in the production of neuron-generated electrical signals. These membrane spanning proteins are therefore essential for neuronal signal transduction, and, accordingly, represent an important class of molecular targets for drug development. These channels may either be voltage-gated or ligand-gated. Examples of the former include voltage-gated sodium and calcium channels, while examples of the latter are members of the inonotropic glutamate receptor family. These molecular targets are of essential importance to pharmacology and therapeutics. Moreover, these ion channels either directly or indirectly lead to calcium signaling events in mammalian cells. The measurement of intracellular calcium transients in living mammalian cells is accordingly an important functional high-throughput assay for identification of agonists and antagonists of receptors or channels of pharmacological interest. Therefore, monitoring intracellular calcium in hESC-derived neurons is a potential new high-throughput tool to better understand, potentially predict, and avoid neurotoxicity in humans. In addition, efforts to develop new agents for neural applications ranging from pain relief to treatment of epilepsy may be enhanced through quantitative analysis of calcium responsiveness of representative human neurons.

Figure 3:
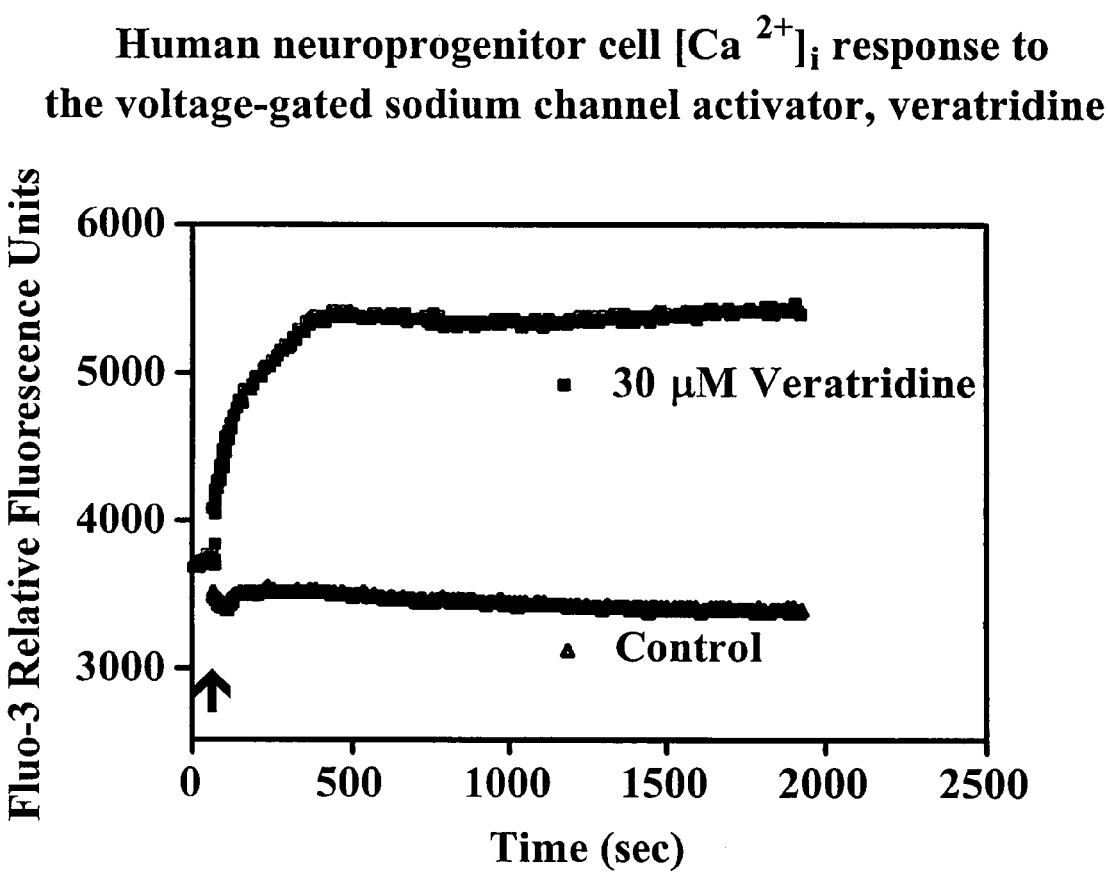
FIG. 3 shows the effects on intracellular calcium concentration to the sodium channel activator veratridine.

In this experiment, human neuroprogenitor cells were seeded in 96-well plates and incubated with dye loading medium containing 2 µM Fluo-3AM and 0.04% pluronic acid in Locke's buffer. After 45 minutes of incubation, the neuroprogenitor cells were gently washed three times in fresh Locke's buffer. Following the final wash, 150 µl of Locke's buffer was added to each well and the plate was transferred to the FLIPRO® incubation chamber (Molecular Devices). The displayed data are from representative wells showing no increase in human neuroprogenitor cell cytoplasmic [$Ca^{2+}$] after addition of Locke's buffer (Control) to the cells, while addition of 30 µM veratridine evoked a reproducible elevation of intracellular [$Ca^{2+}$] approaching 145% of control. These preliminary data indicate that human neuroprogenitor cells express functional voltage-gated sodium channels inasmuch as this ion channel is the molecular target for veratridine. See FIG. 3. These cells can therefore be used to determine the effect of an antagonist or agonist on calcium uptake or whether an agent is a likely antagonist or agonist of calcium uptake.

Neuroprogenitor cells and motor neuron cells according to the present invention may also be used to test the neurotoxicity of a suspect agent. In this method, a sample of feeder cell free neuroprogenitor cells or motor neuron cells is exposed to a suspect agent and compared to control cells to determine whether or not the suspect agent is a neurotoxin and the relative strength of its neurotoxicity.

While the invention has been described hereinabove, care should be taken not to limit the invention in a manner which is unintended and is inconsistent with the invention as set forth in the following claims.

The invention claimed is:

1. A method for producing adherent feeder cell free neuroprogenitor cells, said method comprising the steps of:
   a. contacting adherent primate embryonic stem cells in a serum free differentiation medium consisting essentially of at least the components of a minimum essential medium and basic fibroblast growth factor (bFGF) and optionally non-essential amino acids, leukaemia inhibitory factor (LIF), an antibiotic, mercaptoethanol or another cell medium selected from B27, N2 or mixtures thereof, with an effective amount of at least one differentiation protein to differentiate said adherent primate embryonic stem cells without embryoid cell formation into adherent neuroprogenitor cells which are greater than 90% nestin positive, and which are PSNCAM and A2B5 negative;

b. passaging said neuroprogenitor cells; and c. isolating or collecting said neuroprogenitor cells.

2. The method according to claim 1 wherein said differentiation medium consists essentially of DMEM/F12 (1:1) or neurobasal media and bFGF optionally containing L-glutamine, glucose, at least one antibiotic and optionally, at least one component selected from the group consisting of non-essential amino acids, leukaemia inhibitory factor (LIF), mercaptoethanol and another cell media selected from B27, N2 or mixtures thereof.

3. The method according to claim 1 wherein said embryonic stem cells are human embryonic stem cells.

4. The method according to claim 3 wherein said differentiation medium consists essentially of DMEM/F12 (1:1) and bFGF supplemented with antibiotics, L-glutamine, and N2 and said differentiation protein is laminin or a mixture of laminin and at least one additional differentiation protein.

5. The method according to claim 3 wherein said differentiation medium consists essentially of DMEM/F12 and bFGF supplemented with antibiotics, L-glutamine, leukaemia inhibitory factor, non-essential amino acids and beta mercaptoethanol and said differentiation protein is laminin or laminin and at least one additional differentiation protein.

6. The method according to claim 3 wherein said differentiation medium consists essentially of DMEM/F12 and bFGF supplemented with antibiotics, L-glutamine, non-essential amino acids and beta mercaptoethanol and said differentiation protein is laminin or laminin and at least one additional differentiation protein.

7. The method according to claim 3 wherein said differentiation medium consists essentially of neurobasal medium and bFGF, supplemented with antibiotics, L-glutamine, leukaemia inhibitory factor and B27 and said differentiation protein is laminin or laminin and at least one additional differentiation protein.

8. The method according to claim 3 wherein said human embryonic stem cells are contacted with laminin in a serum-free DMEM/F12 (1:1) differentiation medium supplemented with antibiotics, L-glutamine, leukaemia inhibitory factor, non-essential amino acids and beta mercaptoethanol for a first period of about 3 to 10 days, followed by contacting said cells with laminin in a serum-free DMEM/F12 (1:1) differentiation medium supplemented with antibiotics, L-glutamine, bFGF and N2 for a second period of about 3 to 10 days, followed by contacting said cells with laminin in a serum-free neurobasal medium, supplemented antibiotics, L-glutamine, basic fibroblast growth factor, leukaemia inhibitory factor and B27 for a third period of about 3 to 10 days.

9. The method according to claim 3 wherein said human embryonic stem cells are contacted with laminin in a serum-free DMEM/F12 (1:1) differentiation medium supplemented with antibiotics, fetal bovine serum, knockout serum replacement, L-glutamine, non-essential amino acids and beta mercaptoethanol for a first period of about 3 to 10 days, followed by contacting said cells with laminin in a serum-free DMEM/F12 (1:1) differentiation medium supplemented with antibiotics, L-glutamine, bFGF and N2 for a second period of about 3 to about 10 days, followed by contacting said cells with laminin in a serum-free neurobasal medium, supplemented with antibiotics, L-glutamine, basic fibroblast growth factor, leukaemia inhibitory factor and B27 for a third period of about 3 to about 10 days.

10. The method according to claim 3 wherein said human embryonic stem cells are contacted with laminin in a serum-free DMEM/F12 (1:1) differentiation medium supplemented with antibiotics, L-glutamine, bFGF and N2 for a first period of 7 to about 17 days, followed by contacting said cells with laminin in a serum-free neurobasal medium, supplemented with antibiotics, L-glutamine, basic fibroblast growth factor, leukaemia inhibitory factor and B27 for a second period of about 3 to about 10 days.

11. The method according to claim 3 wherein said human embryonic stem cells are contacted with laminin in a serum-free DMEM/F12 (1:1) differentiation medium supplemented with antibiotics, L-glutamine, leukaemia inhibitory factor, basic fibroblast growth factor, non-essential amino acids and beta mercaptoethanol for a period of about 14 to 30 days.

12. The method according to claim 1 wherein said differentiation protein comprises a protein selected from the group consisting of laminin, tenascin, thrombospondin, collagen, fibronectin, vibronectin, polylysine, polyornithine and mixtures thereof.

13. The method according to claim 3 wherein said differentiation protein comprises a protein selected from the group consisting of laminin, tenascin, thrombospondin, collagen, fibronectin, vibronectin, polylysine, polyornithine and mixtures thereof.

14. A method of producing motor neuron cells comprising exposing neuroprogenitor cells produced according to the method of claim 2 to at least one differentiation protein in a serum-free differentiation medium comprising at least the components of a minimum essential medium, basic fibroblast growth factor and optionally, at least one component selected from the group consisting of non-essential amino acids, an antibiotic, mercaptoethanol, Sonic Hedgehog, retinoic acid, leukaemia inhibitory factor, another cell media selected from B27, N2 or mixtures thereof for a first period of about 1 to 10 days followed by growing said cells obtained from said first period in the absence of basic fibroblast growth factor, Sonic Hedgehog and retinoic acid for a period of about 5 to 20 days; and optionally, isolating or separating said cells.

15. The method according to claim 14 wherein said differentiation protein is laminin or laminin and optionally, at least one additional differentiation protein.

16. A method of producing motor neuron cells comprising exposing neuroprogenitor cells produced according to the method of claim 1 to a differentiation protein in a serum-free differentiation medium comprising at least the components of a minimum essential medium, basic fibroblast growth factor and optionally, at least one component selected from the group consisting of non-essential amino acids, an antibiotic, mercaptoethanol, Sonic Hedgehog, retinoic acid, leukaemia inhibitory factor, another cell media selected from B27, N2 or mixtures thereof for a first period of about 1 to 10 days followed by growing said cells obtained from said first period in the absence of basic fibroblast growth factor, Sonic Hedgehog, and retinoic acid for a period of about 5 to 20 days; and optionally, isolating or separating said cells.

17. A method of producing motor neuron cells comprising exposing neuroprogenitor cells produced according to the method of claim 3 to a differentiation protein in a serum-free differentiation medium comprising at least the components of a minimum essential medium, basic fibroblast growth factor and optionally, at least one component selected from the group consisting of non-essential amino acids, an antibiotic, mercaptoethanol, Sonic Hedgehog, retinoic acid, leukaemia inhibitory factor, another cell media selected from B27, N2 or mixtures thereof for a first period of about 1 to 10 days followed by growing said cells obtained from said first period in the absence of basic fibroblast growth factor, Sonic Hedgehog and retinoic acid for a period of about 5 to 20 days; and optionally, isolating or separating said cells.

18. The method of claim 1, wherein said differentiation medium is a neurobasal medium.

19. The method according to claim 1 wherein said differentiation protein is laminin or laminin and at least one additional differentiation protein.

20. The method according to claim 1 comprising propagating said neuroprogenitor cells after said isolating step.

21. The method according to claim 1 wherein said cells are collected and cryopreserved.

22. The method according to claim 2 wherein said cells are collected and cryopreserved.

23. The method according to claim 3 wherein said cells are collected and cryopreserved.

24. The method according to claim 4 wherein said cells are collected and cryopreserved.

25. The method according to claim 5 wherein said cells are collected and cryopreserved.

26. The method according to claim 6 wherein said cells are collected and cryopreserved.

27. The method according to claim 7 wherein said cells are collected and cryopreserved.

28. The method according to claim 8 wherein said cells are collected and cryopreserved.

29. The method according to claim 9 wherein said cells are collected and cryopreserved.

30. The method according to claim 10 wherein said cells are collected and cryopreserved.

31. The method according to claim 11 wherein said cells are collected and cryopreserved.

32. The method according to claim 12 wherein said cells are collected and cryopreserved.

33. The method according to claim 13 wherein said cells are collected and cryopreserved.

* * * * *